US008396232B2

(12) United States Patent
Thomas

(10) Patent No.: US 8,396,232 B2
(45) Date of Patent: Mar. 12, 2013

(54) SURGICAL CONSOLE OPERABLE TO PLAYBACK MULTIMEDIA CONTENT

(75) Inventor: Roger D. Thomas, Tustin, CA (US)

(73) Assignee: Novartis AG, Basel (CH)

( * ) Notice: Subject to any disclaimer, the term of this patent is extended or adjusted under 35 U.S.C. 154(b) by 1132 days.

(21) Appl. No.: 11/828,040

(22) Filed: Jul. 25, 2007

(65) Prior Publication Data

US 2008/0027574 A1  Jan. 31, 2008

Related U.S. Application Data

(60) Provisional application No. 60/833,207, filed on Jul. 25, 2006.

(51) Int. Cl.
G09F 27/00 (2006.01)

(52) U.S. Cl. .................. 381/124; 606/1; 606/4; 340/500

(58) Field of Classification Search ............. 381/86–87, 381/334, 124, 58; 600/27–28; 606/1, 103, 606/4; 340/500
See application file for complete search history.

(56) References Cited

U.S. PATENT DOCUMENTS

| | | |
|---|---|---|
| 1,847,658 A | 3/1932 | Lasker |
| 3,003,196 A | 10/1961 | Swanson |
| 3,252,623 A | 5/1966 | Corbin et al. |
| 3,266,494 A | 8/1966 | Brownrigg et al. |
| 3,520,071 A | 7/1970 | Clark et al. |
| 3,752,161 A | 8/1973 | Bent |
| 3,815,604 A | 6/1974 | O'Malley et al. |
| 3,842,839 A | 10/1974 | Malis et al. |
| 3,884,238 A | 5/1975 | O'Malley et al. |
| 3,899,829 A | 8/1975 | Storm et al. |
| 3,903,881 A | 9/1975 | Weigl |
| 3,930,505 A | 1/1976 | Wallach |
| 3,977,425 A | 8/1976 | Hayashida |
| 4,007,742 A | 2/1977 | Banko |
| 4,024,866 A | 5/1977 | Wallach |
| 4,168,707 A | 9/1979 | Douvas et al. |
| 4,180,074 A | 12/1979 | Murry et al. |
| 4,217,993 A | 8/1980 | Jess et al. |
| 4,223,676 A | 9/1980 | Wuchinich et al. |
| 4,245,815 A | 1/1981 | Willis |
| 4,314,560 A | 2/1982 | Helfgott et al. |
| 4,320,761 A | 3/1982 | Haddad |
| 4,324,243 A | 4/1982 | Helfgott et al. |
| 4,395,257 A | 7/1983 | Manella |

(Continued)

FOREIGN PATENT DOCUMENTS

| | | |
|---|---|---|
| DE | 2547185 | 4/1977 |
| EP | 1455324 | 9/2004 |

(Continued)

OTHER PUBLICATIONS

International Search Report for PCT/US2007/074334, Publication No. WO2008/014329, 4 pages.

(Continued)

Primary Examiner — Disler Paul
(74) Attorney, Agent, or Firm — Darien Reddick

(57) ABSTRACT

A method and system are disclosed for playing, storing, accessing, and retrieving multimedia content and providing the content to a surgical environment. In particular, the audio playback function can provide a means to play background music in an operating room to provide a soothing and/or entertaining background to the surgical team and/or a patient. Further audio and video playback can provide a walkthrough of preparing surgical cassettes, hand pieces and other consumables used in ophthalmic surgery.

15 Claims, 7 Drawing Sheets

U.S. PATENT DOCUMENTS

| | | |
|---|---|---|
| 4,395,258 A | 7/1983 | Wang et al. |
| 4,428,748 A | 1/1984 | Peyman et al. |
| 4,449,550 A | 5/1984 | Ranalli |
| 4,475,904 A | 10/1984 | Wang |
| 4,493,695 A | 1/1985 | Cook |
| 4,627,833 A | 12/1986 | Cook et al. |
| 4,713,051 A | 12/1987 | Steppe et al. |
| 4,758,238 A | 7/1988 | Sundblom et al. |
| 4,790,816 A | 12/1988 | Sundblom et al. |
| 4,798,580 A | 1/1989 | DeMeo et al. |
| 4,907,973 A | 3/1990 | Hon |
| 4,932,879 A | 6/1990 | Ingenito et al. |
| 5,098,426 A | 3/1992 | Sklar et al. |
| 5,455,766 A | 10/1995 | Scheller et al. |
| 5,704,791 A | 1/1998 | Gillio |
| 5,722,836 A | 3/1998 | Younker |
| 5,766,016 A | 6/1998 | Sinclair et al. |
| 5,769,640 A | 6/1998 | Jacobus et al. |
| 5,791,908 A | 8/1998 | Gillio |
| 5,800,179 A | 9/1998 | Bailey |
| 5,855,553 A | 1/1999 | Tajima et al. |
| 5,910,139 A | 6/1999 | Cochran et al. |
| 6,036,458 A | 3/2000 | Cole et al. |
| 6,059,544 A | 5/2000 | Jung et al. |
| 6,074,213 A | 6/2000 | Hon |
| 6,113,395 A | 9/2000 | Hon |
| 6,126,450 A | 10/2000 | Mukai et al. |
| 6,251,113 B1 * | 6/2001 | Appelbaum et al. .......... 606/107 |
| 6,293,926 B1 | 9/2001 | Sorensen et al. |
| 2001/0016711 A1 | 8/2001 | Sorensen et al. |
| 2001/0020937 A1 | 9/2001 | Rosenberg et al. |
| 2002/0045887 A1 | 4/2002 | DeHoogh et al. |
| 2002/0150262 A1 * | 10/2002 | Carter ............................. 381/86 |
| 2002/0168618 A1 | 11/2002 | Anderson et al. |
| 2003/0055410 A1 | 3/2003 | Evans et al. |
| 2003/0202894 A1 | 10/2003 | Leukanech et al. |
| 2003/0225363 A1 | 12/2003 | Gordon et al. |
| 2004/0106916 A1 * | 6/2004 | Quaid et al. ...................... 606/1 |
| 2004/0253129 A1 | 12/2004 | Sorenson et al. |
| 2005/0065462 A1 | 3/2005 | Nazarifar et al. |
| 2005/0109350 A1 | 5/2005 | Luloh |
| 2005/0142525 A1 | 6/2005 | Cotin et al. |
| 2005/0186098 A1 | 8/2005 | Davis et al. |
| 2006/0136073 A1 * | 6/2006 | Kastigar ........................... 700/1 |
| 2006/0270913 A1 | 11/2006 | Todd |

FOREIGN PATENT DOCUMENTS

| | | |
|---|---|---|
| EP | 1704839 | 9/2006 |
| JP | 03/165759 | 7/1991 |
| JP | 2008/087233 | 4/1996 |
| JP | 11/219100 | 8/1999 |
| JP | 11/231770 | 8/1999 |
| JP | 2000/293095 | 10/2000 |
| JP | 2002-510980 | 4/2002 |
| JP | 2002/511156 | 4/2002 |
| JP | 2005/114764 | 4/2005 |
| WO | WO03081379 A2 | 10/2003 |
| WO | WO 2006/073400 | 7/2006 |
| WO | WO 2007/030877 | 3/2007 |

OTHER PUBLICATIONS

European Search Report for Application No. 10187753.8, 2 pages.
PCT International Preliminary Report on Patentability with Written Opinion of the International Searching Authority, PCT/US2008/082797, May 11, 2010, 5 pages.
International Search Report for PCT/US2008/082797, Publication No. WO2009062031, Published May 14, 2009, 1 page.
Final Office Action, U.S. Appl. No. 11/867,262, May 24, 2011, 19 pages.
Non-Final Office Action, U.S. Appl. No. 11/867,262, Nov. 29, 2010, 15 pages.
European Search Report for Application No. 07117969.1, Publication No. EP1909246, Published Apr. 9, 2008, 1 page.
Supplementary European Search Report for Application No. 08847492.9, Jul. 11, 2012, 4 pages.

* cited by examiner

SURGICAL CONSOLE OPERABLE TO PLAYBACK MULTIMEDIA CONTENT

This application claims priority from the provisional application, U.S. Patent Application Ser. No. 60/833,207 filed Jul. 25, 2006.

TECHNICAL FIELD OF THE INVENTION

The present invention relates generally to surgical console systems and methods, and, more particularly, to a system and method for playing multimedia content in a surgical environment.

BACKGROUND OF THE INVENTION

The human eye can suffer a number of maladies causing mild deterioration to complete loss of vision. While contact lenses and eyeglasses can compensate for some ailments, ophthalmic surgery is required for others. Generally, ophthalmic surgery is classified into posterior segment procedures, such as vitreoretinal surgery, and anterior segment procedures, such as cataract surgery. More recently, combined anterior and posterior segment procedures have been developed.

During modern surgery, particularly ophthalmic surgery, a surgeon may use a variety of pneumatic and electronically driven microsurgical handpieces. The handpieces are typically operated by a microprocessor-driven surgical console that receives inputs from the surgeon or an assistant by a variety of peripheral devices, such as foot pedal controllers, infrared remote control devices and menu-driven touch screens. One such microsurgical console is described in U.S. Pat. No. 5,455,766 (Scheller, et al.), the entire content of which is incorporated herein by reference. Surgical consoles allow surgeons to manually input surgical operating parameters and store these "customized" parameters in the console memory for future use. Typically, the operating parameters and methodologies are inputted manually using, for example, a keypad or a touch screen, or are downloaded from another console that has had the parameters inputted manually.

While in a surgical environment, surgical personnel in a surgical environment routinely play music or have some other form of multimedia content playing in the surgical room as a means to pass the time more pleasantly and to provide soothing or entertaining background noise for themselves and patients. Typically, the music or multimedia content is played using a separate device specifically suited to the purpose and brought into the surgical room as an additional piece of equipment. This results in both additional clutter in a surgical room and in a potential distraction when it is desired to change, start or stop the music or other content. Additionally, various alerts may be associated with the operation of an ophthalmic surgical console during a surgical procedure. The surgical team may have difficulty hearing these alerts when background music is played using a separate playback device.

Accordingly, a need exists for a surgical console that allows for the playback of various multimedia files (content) that may be used to facilitate the surgical procedure.

SUMMARY OF THE INVENTION

The embodiments of the surgical console operable to playback multimedia content of the present invention substantially meet these needs and others. Embodiments of the present invention provide a surgical console operable to play, store, access, and retrieve multimedia content (i.e. audio and video) that may be provided to the surgical team before, during and after a surgical procedure. In particular, the audio playback function can provide a means to play background music in an operating room to provide a soothing and/or entertaining background to the surgical team and/or a patient. Further, audio and video playback can provide a walkthrough of preparing surgical cassettes, hand pieces and other consumables used in ophthalmic surgery.

One embodiment of the surgical console of the present invention can include means for receiving, at a surgical system (console), multimedia content from a mass storage device. This multimedia content may include audio and/or video for entertainment purposes, such as background music, or audio/video describing one or more steps in setting up a consumable based on consumable information. Another embodiment of the invention is directed to a surgical system capable of displaying a video clip or other suitable media file. The video clip may correspond to a consumable or consumable pack which can be scanned or selected by the user or otherwise recognized by the surgical system. The video clip showing the setup instructions may be displayed in one or more ways (e.g., with or without audio, text, graphics, etc.). The surgical system, according to one embodiment can include a display, a recognition device, and a controller operatively coupled to said display and said recognition device, wherein said controller comprises a processor and a computer-readable medium carrying program instructions executable by said processor. The program instructions can comprise, code for receiving an identification of a first consumable pack which contains a set of consumables, code for automatically obtaining consumable information associated with said set of consumables, code for updating settings of said surgical system based on said consumable information and code for displaying on said display content comprising at least a video showing a set of steps in setting up the set of consumables.

In embodiments of the invention, the control of the video clip or other suitable media file can be tailored to suit the various needs, knowledge, and/or skill levels of users. In one embodiment, the surgical system can provide multiple modes: Advanced, Audio, Video, and Wizard. Any one of the modes can be configured as the default mode. In a first mode, a user can skip the playback of the audio/video clip entirely and simply jump to or select a desired point or topic related to a particular instrument or consumable. In a second mode, a user can choose to play the entire clip or file(s) (audio and/or video) without interruption. In a third (e.g., wizard) mode, step-by-step instructions are displayed and, optionally, a user may be required to acknowledge at the completion of each step in order to move forward to the next step in a pre-defined setup sequence.

An advantage provided by the embodiments of the present invention relates to providing a more convenient system and interface for playing audio or other content in a surgical environment, such as for background music during a procedure. Embodiments of this invention operable to provide this advantage can comprise a surgical console including an interface, such as the interfaces commonly found on a compact disc player, DVD player, mp3 player or other such audio/video player as will be familiar to those having skill in the art. Further, embodiments can include an input operable to connect an external player to the surgical console to play selected audio or other multimedia content through the surgical console.

Another advantage provided by embodiments of the present invention relates to a surgical system's ability of facilitating a user to setup complex ophthalmic surgical instrumentation and consumables associated therewith.

Still another advantage provided by embodiments of the present invention relates to a surgical system's flexibility of facilitating diverse users with various levels of skills in setting up complex ophthalmic surgical instrumentation and consumables associated therewith and establishing a calm environment in which the procedure can occur.

Other advantages of the present invention will become more apparent to one skilled in the art upon reading and understanding the detailed description of the preferred embodiments described herein with reference to the following drawings.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGs., like numerals being used to refer to like and corresponding parts of the various drawings.

Figure 1:
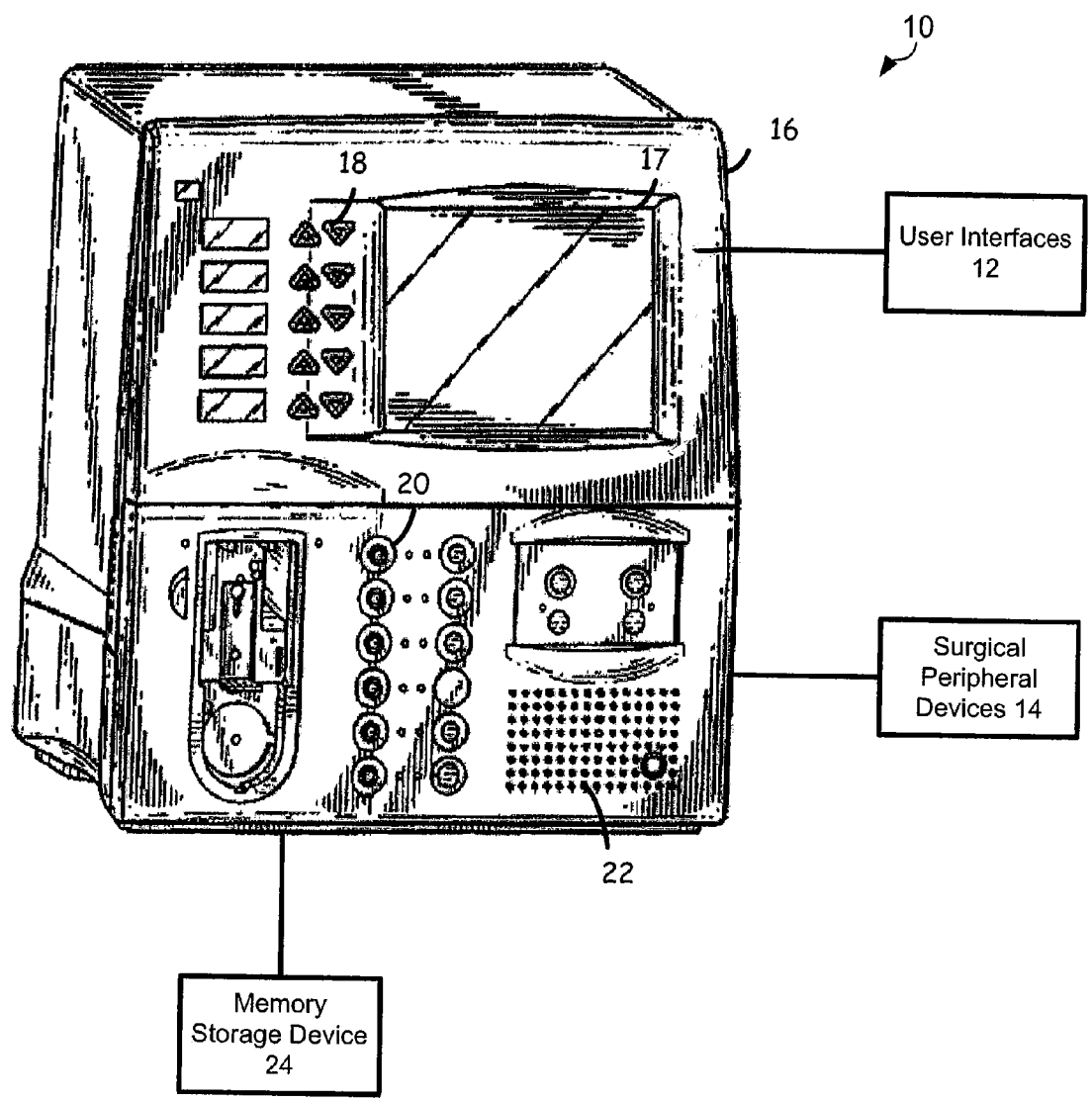
FIG. 1 is a perspective view of one surgical console that may be used with embodiments of the present invention.

An audio and/or multimedia playback device provided by embodiments of the present invention may be implemented as part of any suitable surgical console such as, but not limited to, the Series 2000® Legacy® cataract surgical system, the Infiniti™ Vision System surgical system, or the Accurus® 400VS surgical system, as seen in FIG. 1. These consoles are commercially available from Alcon Laboratories, Inc., of Fort Worth, Tex. For example, these consoles can provide access to various multimedia files stored within memory or storage devices accessible to the surgical console. In a similar manner, audio or multimedia content stored on an external media, such as a compact disk, portable memory device, DVD or mp3 player, can be played through a surgical console embodiment of the present invention.

FIG. 1 is an illustration of a surgical console 10 in accordance with the present invention. Microsurgical Console 10 may operably couple to a number of user interfaces 12, such as a foot pedal assembly, or other push-button type assembly not shown, and to microsurgical peripheral devices 14. Console 10 allows an operator, such as a surgeon, to begin a surgical procedure by setting the initial operating parameters and modes into the console. This may be done by allowing the operator to interface with the surgical console through user interfaces 12 or other interfaces provided on the front panel 16. These may include an electronic display screen 17, a plurality of push-button switches or touch-sensitive pads 18, a plurality of endless digital potentiometer knobs 20, or other like interfaces known to those skilled in the art. The push-buttons 18 and knobs 20 are actuable by an operator to access various different operating modes and functions. Console 10 may also include the ability to accept storage media such as cassette tapes, memory cards, floppy disks, compact discs (CDs), digital video disks (DVDs), or other like devices known to those skilled in the art.

Electronic display screen 17 may be controlled by a processing module that allows the operator access to one or more different menus or messages that relate to the functions and operations of the various push buttons 18 and knobs 20. In one embodiment, the display screen 17 may be divided into display screen regions associated with individual push buttons 18. This arrangement allows for the indicated function of each button 18 or knob 20 to be readily changed. Additionally, the use of the electronic display screen 17 also permits the buttons 18 and knobs 20 to be labeled in virtually any language.

Microsurgical console 10 may be adapted for use with a number of different surgical instruments (i.e., microsurgical peripheral devices 14). For example, these may include a fiber optic illumination instrument, a fragmentation emulsification instrument, a cutting instrument, such as a guillotine cutter for vitrectomy procedures, and/or micro-scissors inset for proportionate and multiple cutting. While the above-identified microsurgical instruments are provided for illustrative purposes, it should be understood that the microsurgical console 10 can be used with other similar equipped instruments.

In general, any microsurgical instruments that are actuated or controlled by pneumatic or electronic signals may be operably coupled to and controlled by console 10. This control or actuation may be governed by pneumatic, electronic, optical, or other like signals known to those skilled in the art wherein the signals are generated or provided by console 10. Each of these illustrated microsurgical devices that couple to console 10 may have different modes of operation that may require different settings or parameters that are provided by the microsurgical console 10. By saving these operating parameters and surgical modes that are associated with specific steps of a surgical procedure in memory, the setup of the microsurgical peripheral devices 14 is facilitated by eliminating the often tedious or cumbersome process of initializing these devices manually via the surgical console 10 for each step of a surgical procedure.

As the operator/surgeon advances through a surgical procedure, pertinent changes to the operating modes and peripheral device operating parameters are accessed from console memory and used to initialize or setup the microsurgical devices for individual steps within an overall surgical procedure. At the completion of a surgical procedure, the completed surgical procedure may be saved as a recorded procedure in memory coupled to console 10. It should be noted that within surgical console 10 is a processing module coupled to memory where the processing module is operable to execute steps that will be discussed in the logic flow diagrams herein.

Additionally, surgical console 10 may include a microphone and/or speaker 22. Further, surgical console 10 may be coupled to a mass storage device 24. This mass storage device may take the form of an external digital playback device such as an MP3 player, a compact disc external to the microsurgical console 10 or within that microsurgical console 10, digital video disc, or other mass storage device that may support the retrieval of multi-media information to be presented using microsurgical console 10. The retrieval and playback of the multi-media may be done through the display screen 17 and associated buttons 18 or through dedicated buttons 18 and knobs 20 that relate to specific functions associated with the playback of information.

Figure 2:
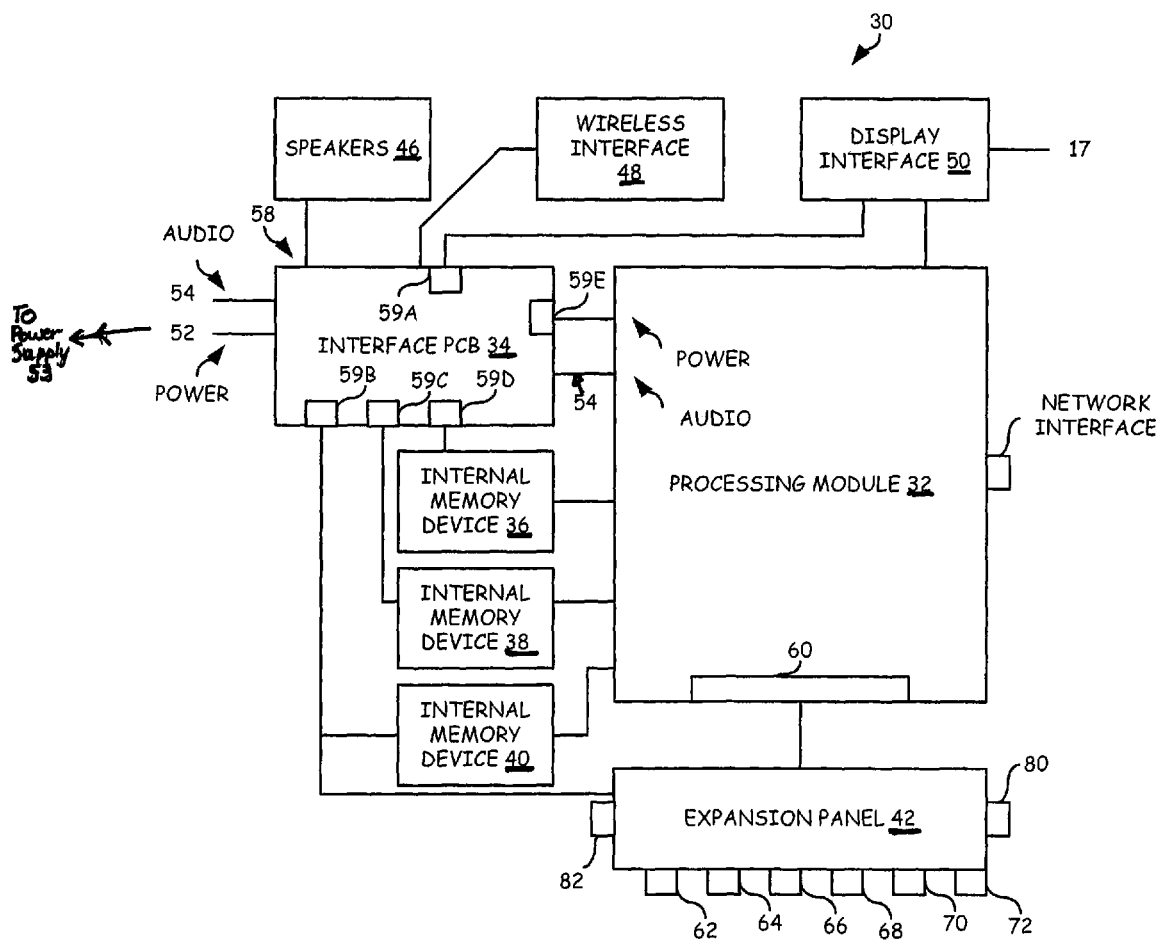
FIG. 2 is a functional block diagram of one surgical console in accordance with embodiments of the present invention.

FIG. 2 depicts a block diagram of various functional modules that may be located within a surgical console 10 of this invention. Host multimedia module 30 of console 10 may functionally include a processing module 32, a power signal 52 provided to input-output (I/O) interface printed circuit board (PCB) 34, mass storage devices 36, 38, and 40, speaker(s) 46, display interface 50, expansion panel 42, and an external connection to audio inputs. Interface PCB 34 may include an audio output 58, a power output 59 (functionally distributed as power outputs 59A-59E), and audio input(s) 54.

Interface PCB 34 couples to an external or internal power supply 53 (not shown). Then interface PCB 34 may distribute power to various other elements contained within various other functional elements of surgical console 10. For example, power may be distributed through connections 59A, 59B, 59C, 59D and 59E to processing module 32, mass storage devices 36-40, expansion panel 42, and other functional units within the surgical console 10 as required. Additionally, interface PCB 34 may receive audio signals through audio ports 54 that may be for external connections with which to receive audio signals, or connections to processing system 32 that provide audio signals that interface PCB 34 may route to audio output port 58 and speakers 46. Mass storage devices 36-40 may further include hard drives, DVD drives, CD drives, and other like drives.

Power is supplied by the interface PCB 34 to these mass storage devices, wherein the multimedia content contained therein or other information contained therein may be accessed through various interfaces to processing module 32 and then routed to an appropriate playback portion of the surgical console through, for example, interface PCB 34. For example, the audio signal may be routed to a speaker in the case of a digital audio file such as an MP3 file, wave file or other like file or to display module 17 in the case of video or image content. Thus, interface PCB 34 can process and playback audio or video files from internal mass storage devices 36-40, which can contain multi-media files to be played back during a surgical procedure. Also, an external multi-media playback device such as, but not limited to, an MP3 player, CD player or DVD player may be coupled to the interface PCB 34 and provide audio and/or video signals to the interface PCB 34 which may then be processed using processing module 32 and presented using the appropriate playback means, such as speakers 46 or display module 17. Additionally, control devices such as a keyboard or mouse may be coupled to interface PCB 34 as a user interface to control the playback of the multi-media files. Otherwise, native controls such as buttons 18 and/or knobs 20, that may have functions defined as presented in display 17, may be used to control the playback of the multi-media content.

Processing module 32 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The memory, such as internal mass storage devices 36-40, may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processing module 32 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The memory stores, and the processing module executes, operational instructions corresponding to at least some of the steps and/or functions illustrated in the FIGs.

Figure 3:
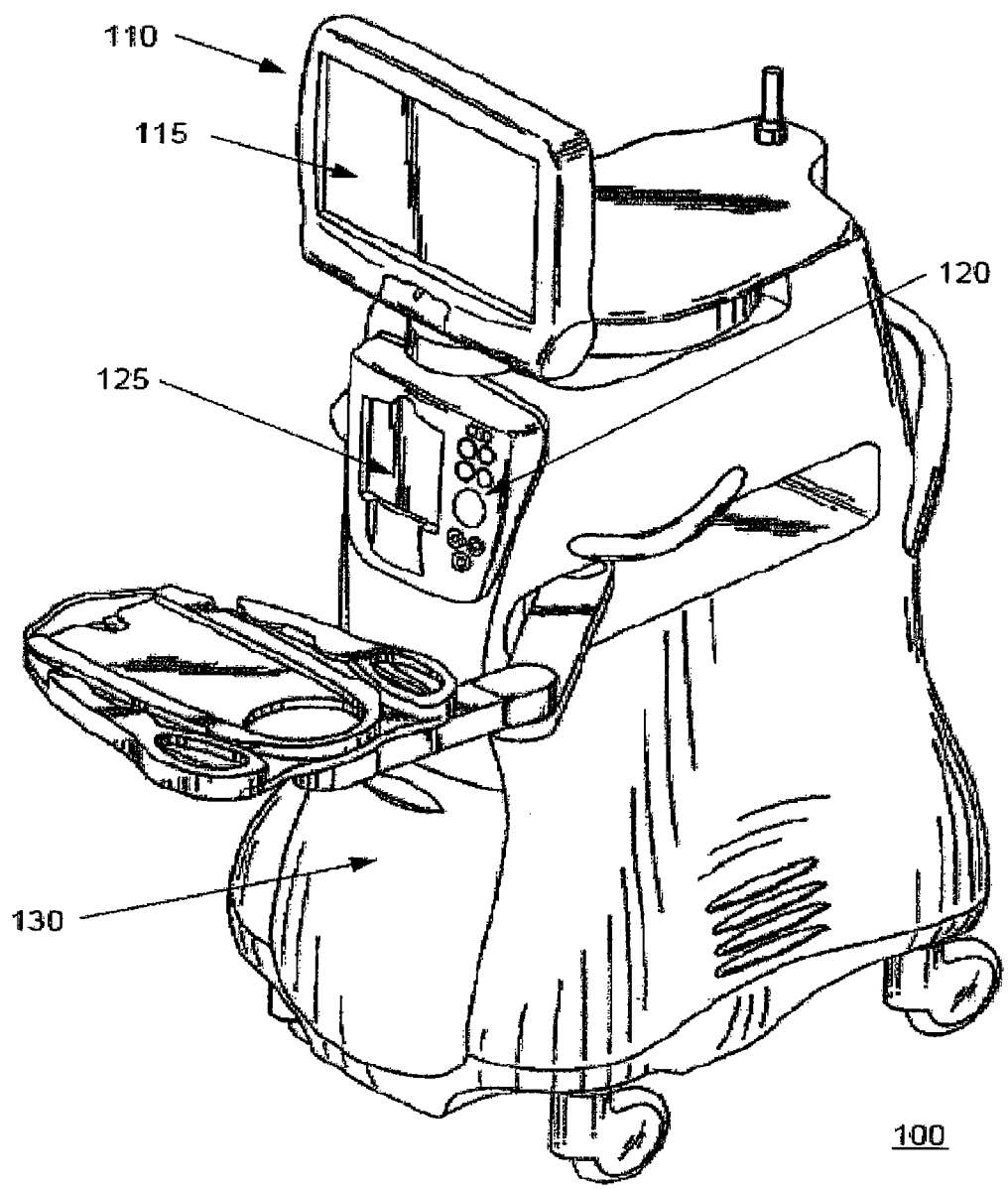
FIG. 3 is a perspective view of one surgical console in accordance with embodiments of the present invention.
Figure 4:
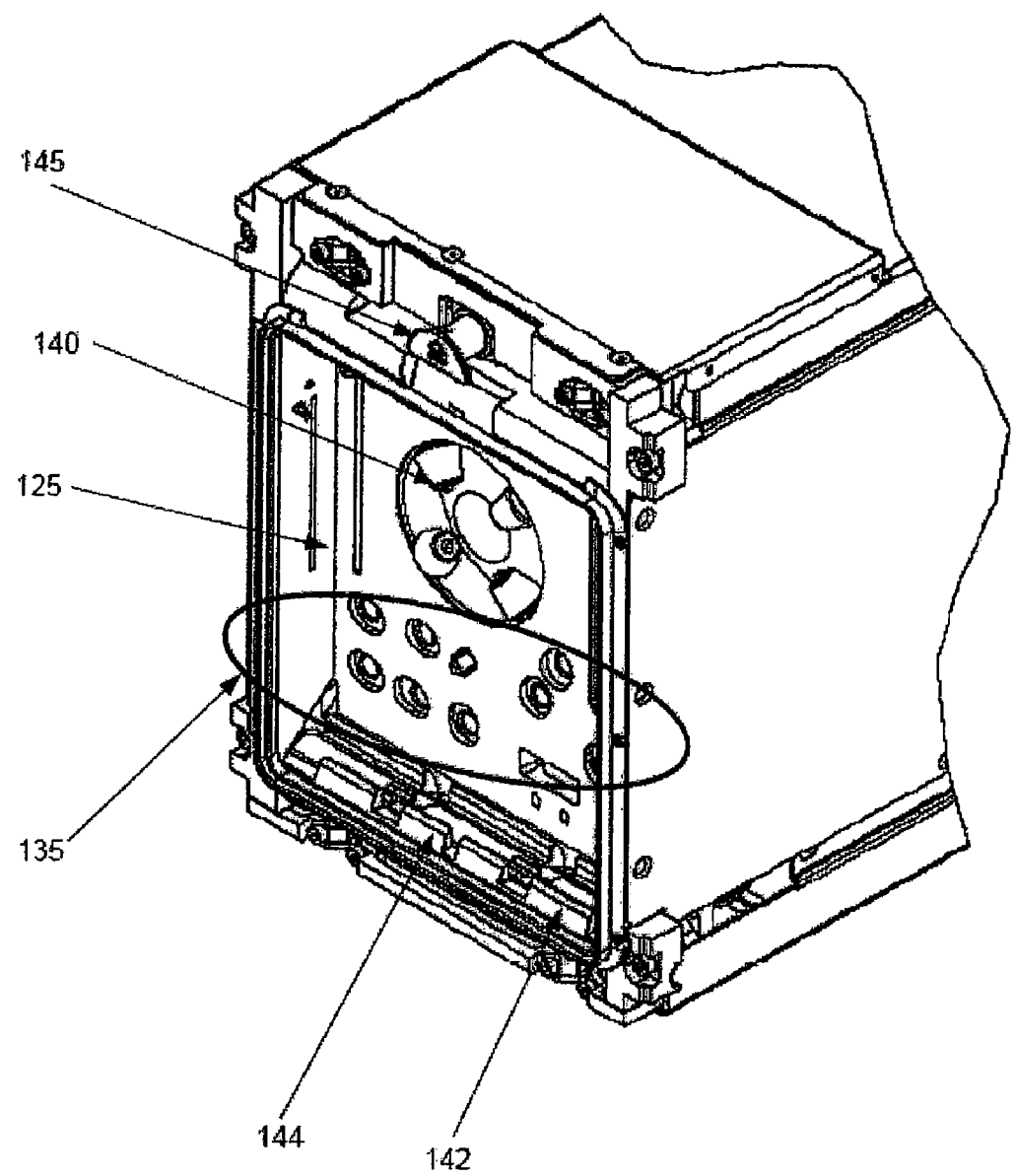
FIG. 4 is a perspective view of one surgical console surgical cassette receiver in accordance with embodiments of the present invention.
Figure 5:
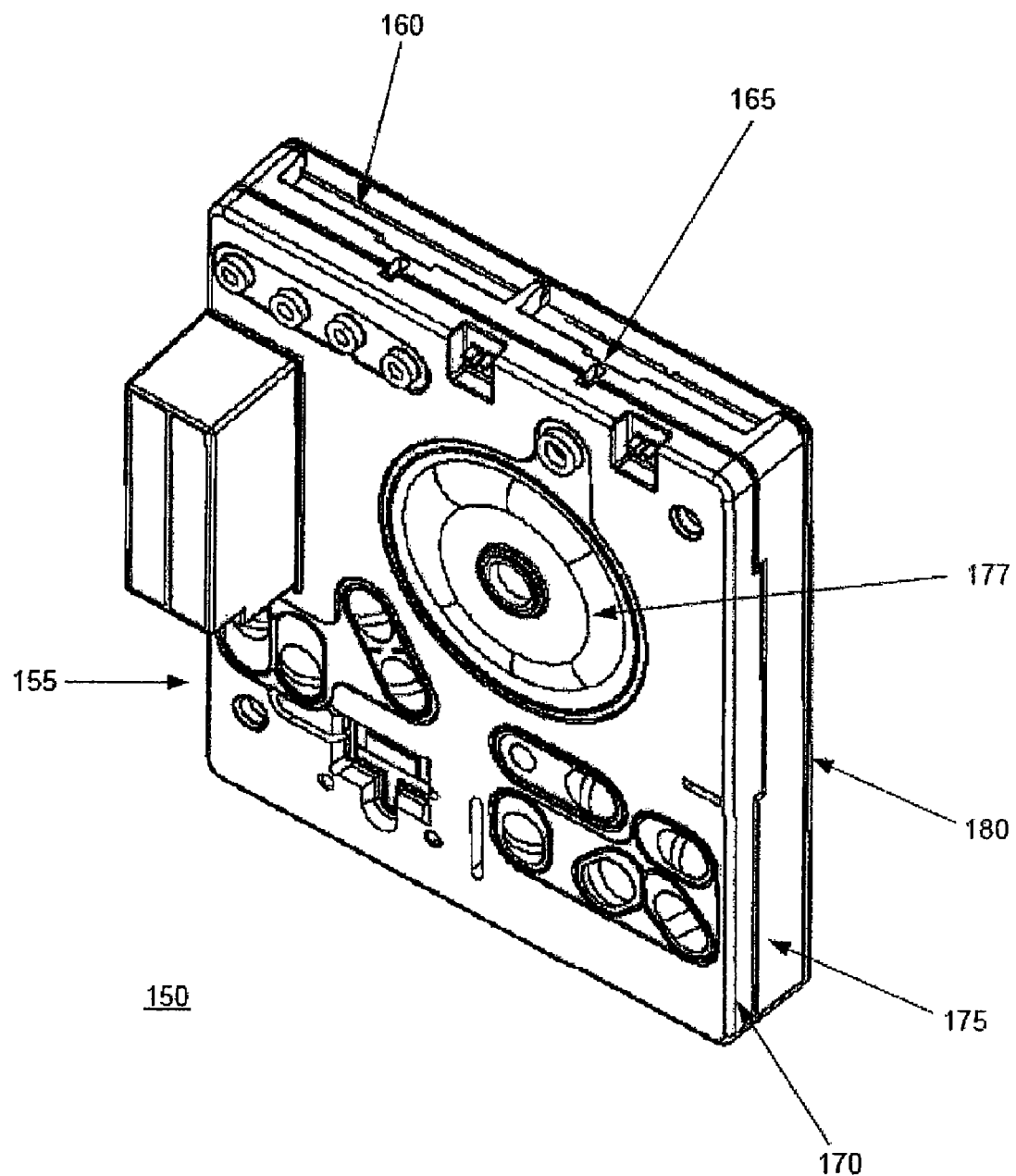
FIG. 5 is a diagrammatic representation of one embodiment of a surgical cassette employed by a surgical console in accordance with embodiments of the present invention.

FIGS. 3-5 illustrate one example of a surgical system and a related consumable, in this case a cassette. These drawings exemplify a surgical environment in which embodiments of the present invention may be implemented. It can be seen from FIGS. 3-5 that a surgical console acts in cooperation with a number of consumables that may require setup before a surgical procedure takes place. Embodiments of the present invention provide a system and method for facilitating surgical procedures with video and multimedia content displayed on or played back with a surgical console. As described further below, the console can recognize the consumables to be used through a variety of mechanisms and play the appropriate content for the user to aid the user in setting up the consumables. Through the use of videos and other multimedia content, the present invention provides a mechanism that substantially facilitates surgical procedures, or at least substantially reduces the shortcomings of previous methods.

One embodiment of the invention is directed to a surgical system capable of displaying a video clip, audio file, or other suitable media file. The invention and various features and advantageous details thereof are explained more fully with reference to the exemplary, and therefore non-limiting, embodiments illustrated in the accompanying drawings and detailed in the following description. Descriptions of known programming techniques, computer software, hardware, operating platforms and protocols may be omitted so as not to unnecessarily obscure the invention in detail. It should be understood, however, that the detailed description and the specific examples, while indicating the preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

FIG. 3 is a diagrammatic representation of one embodiment of an ophthalmic surgical console 100. Surgical console 100 can include a swivel monitor 110 that has touch screen 115. Swivel monitor 110 can be positioned in a variety of orientations for whomever needs to see touch screen 115. Swivel monitor 110 can swing from side to side, as well as rotate and tilt. Touch screen 115 provides a graphical user interface ("GUI") that allows a user to interact with console 100.

Surgical console 100 also includes a connection panel 120 used to connect various tools and consumables to surgical console 100. Connection panel 120 can include, for example, a coagulation connector, balanced salt solution receiver, connectors for various hand pieces and a fluid management system ("FMS") or cassette receiver 125. Surgical console 100 can also include a variety of user friendly features, such as a foot pedal control (e.g., stored behind panel 130) and other features. In operation, a cassette (not shown) can be placed in cassette receiver 125. Clamps in surgical console 100 clamp the cassette in place to minimize movement of the cassette during use. The clamps can clamp the top and bottom of the cassette, the sides of the cassette or otherwise clamp the cassette.

Surgical console 100 is provided by way of example and embodiments of the present invention can be implemented with a variety of surgical systems. Example surgical systems in which cassettes according to various embodiments of the present invention can be used include, for example, the Series 2000® Legacy® cataract surgical system, the Accurus® 400VS surgical system, and the Infiniti™ Vision System surgical system, all available from Alcon Laboratories Inc. of Fort Worth, Tex. Additionally, embodiments of the present invention can be used with a variety of surgical cassettes, examples of which are described in U.S. Pub. Nos. 2005/0186098 (application Ser. No. 11/114,289 to Davis et al.), 2004/0253129 (application Ser. No. 10/891,642 to Sorensen et al.), 2005/0065462 (application Ser. No. 10/979,433 to Nazarifar et al.), 2003/0225363 (application Ser. No. 10/156,175 to Gordon et al.), 2001/0016711 (application Ser. No. 09/846,724 to Sorensen et al.) and U.S. Pat. Nos. 6,293,926 to Sorensen et al., 4,493,695 to Cook, 4,627,833 to Cook, 4,395,258 to Wang et al., 4,713,051 to Steppe, et al., 4,798,850 to DeMeo, et al., 4,758,238 to Sundblom et al., 4,790,816 to Sundblom et al., 6,036,458 to Cole et al., and 6,059,544 to Jung et al., each of which is hereby fully incorporated by reference herein. Embodiments of the present invention can be implemented for other suitable surgical systems and cassettes as would be understood by one of ordinary skill in the art.

FIG. 4 is a diagrammatic representation of one embodiment of cassette receiver 125 without a cassette. Cassette receiver 125 can have various input and output ports (indicated generally at 135) to receive fluids (i.e., liquids and gasses) from the surgical cassette. Cassette receiver 125 can further include an opening to allow peristaltic pump rollers 140 to contact the surgical cassette during operation. One embodiment of a peristaltic pump and complimentary cassette is described in U.S. Pat. No. 6,293,926 to Sorensen, which is hereby fully incorporated by reference herein.

The surgical cassette, in the embodiment of FIG. 4, is held in place by a clamp having a bottom rail 142 and a top rail (not shown). Each rail can have clamping fingers (e.g., clamp finger 144) that contact the cassette in corresponding clamping zones. One embodiment of a surgical cassette clamp is described in United States Patent Application Publication No. 2003/0202894 (Ser. No. 10/132,797 to Leukanech, et al.), which is hereby fully incorporated by reference herein. A release button 145 is pressed to initiate release of the cassette from the clamp. Depending on the surgical console 100, the cassette release process can include several steps, including venting of pressure or fluids, disengaging the clamps or other steps. The configuration of FIG. 4 is provided by way of example. The form factor of cassette receiver 125, placement and number of input/output ports and other features of cassette receiver 125 can depend on the surgical console 100, on the surgical procedure being performed or on other factors.

FIG. 5 is a diagrammatic representation of one embodiment of a surgical cassette 150. Cassette 150 can provide a closed system fluidic device that can be discarded following a surgical procedure. Cassette 150 can include a cassette body 155 and clamp receiving portions (e.g., indicated generally at clamping zones 160 and 165) projecting from the cassette body 155. In the embodiment shown, cassette 150 is formed from three primary sections: an inner or surgical console interface section 170 that faces the surgical console when cassette 150 is inserted into surgical console 100, a middle section 175 and a back plate 180. The various sections of cassette 150 can be coupled together via a press fit, interlocking tabs, chemical bonding, thermal bonding, mechanical fasteners or other attachment mechanism known in the art.

Surgical console interface section 170 can provide an interface for fluid flow channels (e.g., flow channel 177 for the peristaltic pump provided by an elastomeric pump membrane), valves (e.g., irrigation/aspiration valves), pressure sensors and other features to manage fluid flow. Cassette 150 can also attach to a fluid bag (not shown) to collect fluids during a procedure.

Figure 6:
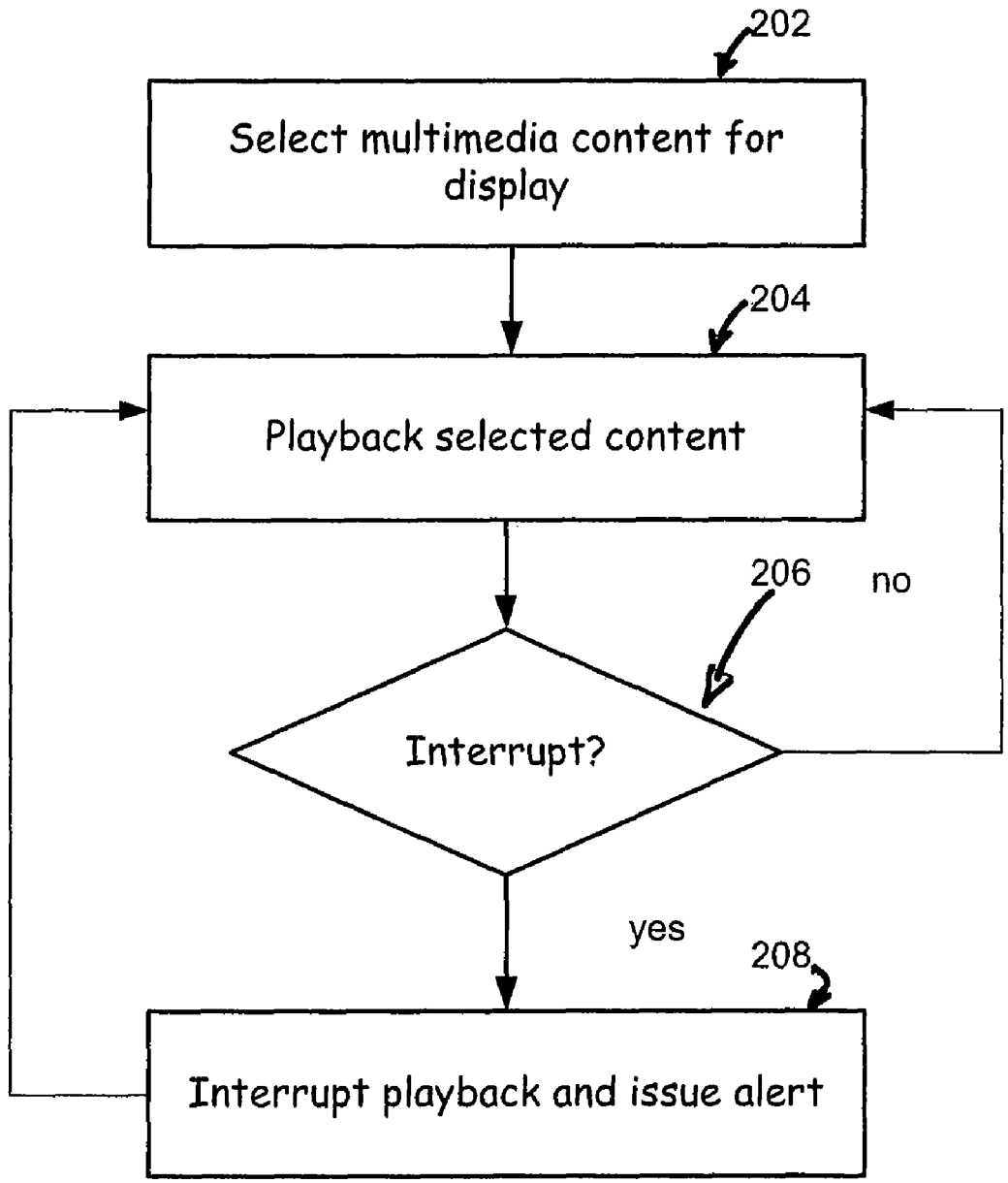
FIG. 6 provides a logic flow diagram associated with one embodiment of the present invention that allows for the playback of multimedia content files such as audio files, MP3 files or other audio content during a surgical procedure.

FIG. 6 provides a logic flow diagram associated with one embodiment of the present invention that allows for the playback of multimedia content files such as audio files, MP3 files or other audio content during a surgical procedure. During normal operation of a surgical procedure, a member of the surgical team may, at step 202, select multimedia content for display. (i.e., a user may select a series of audio files to be played back during the surgical procedure.) These files or sources, once selected from either an internal or external source, may be provided, at step 204, to the surgical room/team using speakers of the surgical console or speakers coupled to the surgical console. The processing system of the surgical console may continually monitor the operating parameters associated with the surgical procedure. At decision point 206, a determination is continuously made as to whether or not an interrupt condition exists requiring that an alert be issued to the surgical team of a condition requiring their attention. This interrupt or alert notifies the surgical team of a specific step, a specific parameter, or an abnormality associated with parameters of the surgical procedure. Should no such interrupt condition exist, the playback may continue by returning to step 204. Otherwise, at step 208, the surgical console may interrupt the playback of the selected multimedia content and issue an interrupt to the surgical team to make them aware of specific conditions associated with the surgical procedure.

Existing surgical consoles do not offer the ability to play background audio files during surgical procedures. Thus surgical teams often use a separate playback device to provide background music during the surgical procedure. However should an audible alarm or condition not be heard on an existing surgical console due to the playback of other audio devices within the surgical theater, important data or changes in operating parameters may not be acted on in a timely manner. Embodiments of the present invention provide the playback of selected multimedia files or other content routed through the surgical console to ensure that the surgical team is alerted to changing operating parameters. This is an important advantage over the ability offered in prior art surgical consoles.

Figure 7:
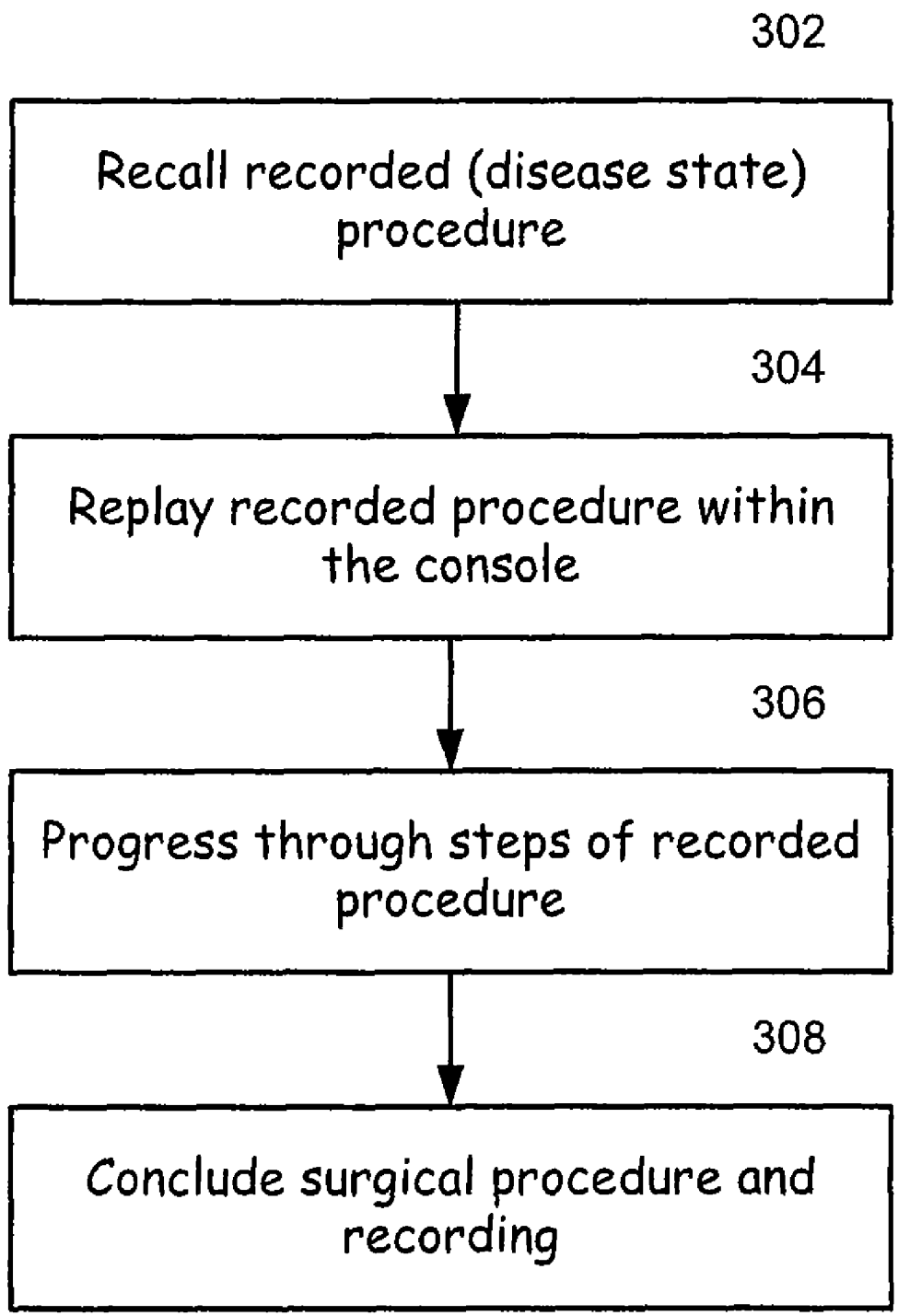
FIG. 7 provides a logic flow diagram associated with one embodiment of the present invention that allows for executing a recorded surgical procedure and for the playback of multimedia content files such as audio files, MP3 files or other audio content during a surgical procedure.

FIG. 7 provides a logic flow diagram illustrating one method by which a recorded surgical procedure may be executed within a surgical console operable to simultaneously playback background multimedia. At Step 302, an operator recalls a recorded procedure. This may be done by using an interface, such as the electronic display screen 17 of the surgical console 10, push buttons 18, a voice or audio interface, or other like means known to those having skill in the art. One embodiment may allow the operator to recall the recorded procedure by specifically pressing a touch-button associated with the name of the surgical procedure to be utilized. Other background content may be similarly selected. A console plays the previously recorded surgical procedure at Step 304 and as it replays this previously recorded surgical procedure, the recorded surgical procedure can be operable to initialize the surgical console. At Step 306, the operator progresses through the steps of the recorded procedure. At any time during the playback, as depicted in FIG. 6, the surgical console may interrupt selected background audio content when user attention or action is required. This may be done using a user interface, such as a voice switch and confirm with audio prompts, in order to inform the operator of changes associated with selected procedural steps. The operator proceeds through the steps of the recorded surgical procedure until completion of the case (at steps 306 and 308).

As illustrated in the procedure of FIG. 7, when a surgeon wants to use a previously recorded procedure, the surgeon recalls the recorded procedure from the console 10 memory and initializes the procedure. The recorded procedure can then automatically adjust the settings and operating parameters of the console 10 as required by the surgical flow. Scrolling through the various steps in the procedure can be accomplished by use of the console footswitch, remote control or console touch screen. The commands may be confirmed via voice confirmation, visual confirmation or other audio-visual or tactile means by the console.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention is described in detail, it should be understood that various changes, substitutions and alterations can be made hereto without departing from the spirit and scope of the invention as described by the appended claims.

What is claimed is:

1. A surgical console, comprising:
   a processing module operable to direct operation of devices operably coupled to the surgical console;
   at least one memory device operably coupled to the processing module, wherein the at least one memory device is operable to store content; and
   a user interface, wherein the user interface allows operators to:
      select content on the memory device for playback; and
      playback the selected content,
   wherein the processing module is operable to interrupt playback of the selected content during a surgical procedure when an operating parameter and surgical mode compares unfavorably to an expected operating parameter and surgical mode associated with the surgical procedure.

2. The surgical console of claim 1, further comprising an external interface operably coupled to the processing module, wherein the external interface is operable to interface the surgical console to an external media source.

3. The surgical console of claim 2, wherein the external media source is a compact disc player, a DVD player or an mp3 player, and wherein the external media source is operable to play content via a surgical console output device.

4. The surgical console of claim 3, wherein the surgical console output device is a surgical console speaker.

5. The surgical console of claim 1, wherein the processing module is operable to monitor operating parameters and surgical modes associated with a surgical procedure.

6. The surgical console of claim 1, wherein the processing module is operable to:
   alter operating modes of devices operably coupled to the surgical console; or
   alter peripheral device operating parameters of devices operably coupled to the surgical console.

7. A method for performing a surgical procedure using a surgical console, comprising:
   selecting a recorded surgical procedure to be performed, the recorded surgical procedure comprising recorded operating parameters and surgical modes of an actual surgical procedure;
   retrieving the recorded surgical procedure from memory;
   utilizing the recorded surgical procedure to perform the surgical procedure;
   selecting multimedia content for playback during the surgical procedure;
   retrieving the multimedia content;
   presenting the multimedia content during the surgical procedure
   monitoring operating parameters and surgical modes associated with the surgical procedure;
   comparing the monitored operating parameters and surgical modes with expected operating parameters and surgical modes associated with the surgical procedure; and
   interrupting playback of the multimedia content during the surgical procedure when the monitored operating parameters and surgical modes compare unfavorably to the expected operating parameters and surgical modes associated with the surgical procedure.

8. The method of claim 7, further comprising:
   alerting users when the monitored operating parameters and surgical modes compare unfavorably to the expected operating parameters and surgical modes associated with the surgical procedure.

9. The method of claim 7, wherein the operating parameters and surgical modes associated with the surgical procedure(s) comprise a series of surgical steps operable to:
   alter operating modes of devices operably coupled to the surgical console; or
   alter peripheral device operating parameters of devices operably coupled to the surgical console.

10. The method of claim 7, wherein the surgical procedure is ophthalmic surgical procedure.

11. The method of claim 7, wherein the operating parameters and surgical modes associated with the surgical procedure(s) comprise:
   pneumatic and electronic parameters associated with surgical peripheral devices operably coupled to the surgical console.

12. A surgical console, comprising:
a processing module operable to:
  direct operations of peripheral devices operably coupled to the surgical console; and
  monitor operating parameters and surgical modes associated with a surgical procedure;
at least one memory device operably coupled to the processing module, wherein the at least one memory device is operable to store surgical procedures and multimedia content;
an external interface operably coupled to the processing module, wherein the external interface is operable to interface the surgical console to an external multimedia source; and
a user interface, wherein the user interface allows operators to:
  initialize the surgical console for a surgical procedure;
  select the surgical procedure to be executed;
  playback the selected surgical procedure;
  select multimedia content for playback; and
  playback the selected multimedia content,
  wherein the processing module is operable to interrupt playback of the selected multimedia content during the surgical procedure when an operating parameter and surgical mode compares unfavorably to an expected operating parameter and surgical mode associated with the surgical procedure.

13. The surgical console of claim 12, wherein the processing module is operable to:
  alter operating modes of devices operably coupled to the surgical console; or
  alter peripheral device operating parameters of devices operably coupled to the surgical console.

14. The surgical console of claim 12, wherein the surgical procedure is ophthalmic surgical procedure.

15. The surgical console of claim 12, wherein the operating parameters and surgical modes associated with the surgical procedure(s) comprise:
  pneumatic and electronic parameters associated with surgical peripheral devices operably coupled to the surgical console.

* * * * *